(12) United States Patent  
Yan

(10) Patent No.: US 7,212,692 B2
(45) Date of Patent: May 1, 2007

(54) MULTIPLE ARRAY SURFACE PLASMON RESONANCE BIOSENSOR

(75) Inventor: Ming Yan, 2809 Elsnab Ct., Pleasanton, CA (US) 94588

(73) Assignee: Ming Yan, Pleasanton, CA (US)

( * ) Notice: Subject to any disclaimer, the term of this patent is extended or adjusted under 35 U.S.C. 154(b) by 9 days.

(21) Appl. No.: 10/704,861

(22) Filed: Nov. 10, 2003

(65) Prior Publication Data

US 2005/0018949 A1 Jan. 27, 2005

Related U.S. Application Data

(60) Provisional application No. 60/424,966, filed on Nov. 8, 2002.

(51) Int. Cl.
*G02B 6/00* (2006.01)
(52) U.S. Cl. .............................. 385/12; 385/14; 385/27; 385/131
(58) Field of Classification Search ................... 385/12, 385/14, 131
See application file for complete search history.

(56) References Cited

U.S. PATENT DOCUMENTS 5,606,633 A 2/1997 Groger et al.
5,623,571 A 4/1997 Chou et al.
2003/0095735 A1* 5/2003 Whateley ...................... 385/12
2003/0206708 A1* 11/2003 Estes et al. ................. 385/130

OTHER PUBLICATIONS

J. Dostalek, J. Lýtyroký, J. Homola, E. Brynda, M. Skalsky, P. Nekvindova, J. Nekvindova, J. Spikova, J. Skvor, & J. Schrofel, Surface Plasmon resonance biosenor based on integrated optical waveguide, Sensors and Actuators B vol. 76, Jun. 1, 2001, pp. 8-12.
A.V. Kabashin & P.I. Nikitin, Surface plasmon resonance interferometer for bio- and chemical-sensors. Optical Communications, vol. 150, May 1, 1998, pp. 5-8.
P.I. Nikitin, A.A. Beloglazov, V.E. Kochergin, M.V. Valeiko, T.I. Ksenevich Surface plasmon resonance inteferometry for biological and chemical sensing Sensors and Actuators B, vol. 54, Jan. 25, 1999, pp. 43-50.
A.V. Kabashin, V.E. Kochergin, P.I. Nikitin, Surface plasmon resonance bio-and chemical sensors with phase-polarisation contrast. Sensors and Actuators B, vol. 54, Jan. 25, 1999, pp. 51-56.

* cited by examiner

*Primary Examiner*—Sung Pak
*Assistant Examiner*—James D. Stein

(57) ABSTRACT

An integrated optical waveguide based surface plasmon resonance biosensor is formed by detecting amplitude and phase of electromagnetic waves utilizing interferometry and/or optical delay configurations.

17 Claims, 9 Drawing Sheets

MULTIPLE ARRAY SURFACE PLASMON RESONANCE BIOSENSOR

RELATED APPLICATION

This application claims the benefit of U.S. Provisional Application No. 60/424966, filed Nov. 8, 2002, and entitled, "Multiple Array Surface Plasmon Resonance Biosensor," which is incorporated herein by this reference.

BACKGROUND OF THE INVENTION

1. Field of the Invention

The present invention relates to biosensors based on integrated optical waveguides, and more particularly, to surface plasmon resonance interferometric detection sensors formed by an array of planar waveguides.

2. Description of Related Art

Surface plasmon resonance (SPR) devices have shown high sensitivity in the detection of chemical and biological agents. Conventional SPR devices are based on sensing the reflectance change of mono- or polychromatic light, which undergoes total internal reflection at the hypotenuse of a prism, which is coated with a thin metal film. At certain angles of incidence for a given wavelength of light, the incident light with polarization in the plane of incidence is in resonance with the surface plasmon of the metal film. The term "surface plasmon" describes the collective longitudinal oscillation of the electrons in the metal film. The angle of incidence for the wavelength of the light at which this surface plasmon resonance occurs is very sensitive to the dielectric constant of the immediate environment of the thin metal film, which can be changed by a change in the index refraction of the surrounding material or chemical bonding of material deposited onto the metal layer.

Free space SPR interferometry techniques, such as SPR ellipsometry, optical heterodyning, and mapping the spatial intensity distribution, are cumbersome to be incorporated into compact SPR devices and exhibit high sensitivity to changes in the environment, such as temperature fluctuations. By contrast, a planar optical waveguide based SPR sensor operates similarly as a free space prism SPR device, but it offers higher sensitivity and is capable of being fabricated into multiple sensors on a single chip and can be easily integrated with fiber optical components, such as light sources and detectors.

Background information on a waveguide based SPR sensors that monitors the ratio of the transverse magnetic (TM) polarization and transverse electric (TE) polarization intensities is described in U.S. Pat. No. 5,606,633, issued Feb. 25, 1997, to Groger et al. "Chemical detector employing surface plasmon resonance excited using an optical waveguide configuration as an asymmetric waveguide coupler," including the following, "the ratio of the TM and TE polarization intensities is monitored by a polarization beam splitter. The relatively unchanged TE polarization intensity serves as an integral reference for the sensor."

The article "Surface plasmon resonance biosensor based on integrated optical waveguide" by J. Dostalek et al. (*Sensors and Actuators*, vol. B76, 2001, pages 8–12) describes the use of a broadband light source combined with spectral interrogation of SPR and demonstrates a detection sensitivity of $10^{-6}$ to a change in the index of refraction. Another SPR technology is based on detecting the phase-change of the light in a SPR sensor, which has been shown to significantly increase the detection sensitivity (P. Nikitin et al, "Surface plasmon resonance interferometer for biological and chemical sensing" *Sensors and Actuators* B., 1999, vol. 54, pp. 43–50).

Accordingly, a need exists to provide a highly sensitive surface plasmon waveguide arrayed sensor that simultaneously detects intensity and phase by planar light wave geometries. The present invention is directed to such a need.

SUMMARY OF THE INVENTION

Accordingly, the present invention provides a highly sensitive surface plasmon waveguide apparatus arranged in a planar waveguide Mach Zehnder based configuration for measuring adsorbed monolayers of predetermined solutions.

Another aspect of the present invention is to provide a highly sensitive surface plasmon waveguide sensor apparatus arranged in a planar waveguide optically delayed waveguide based configuration for measuring adsorbed monolayers of predetermined solutions.

A final aspect of the present invention is to provide a highly sensitive surface plasmon waveguide sensor apparatus arranged as an array of wave-guide surface plasmon resonance (SPR) sensors operatively coupled to optical waveguide arrayed gratings for measuring adsorbed monolayers of predetermined solutions.

Accordingly, the present invention provides a highly sensitive waveguide sensor capable of measuring one or more monolayers of bio-agents and/or chemical agents for immunoassay or other receptor and analyte reactions.

BRIEF DESCRIPTION OF THE DRAWINGS

The accompanying drawings, which are incorporated into and constitute a part of the specification, illustrate embodiments of the invention and, together with the general description of the invention given above, and the detailed description of the specific embodiments, serve to explain the principles of the invention.

DETAILED DESCRIPTION OF THE INVENTION

Figure 1:
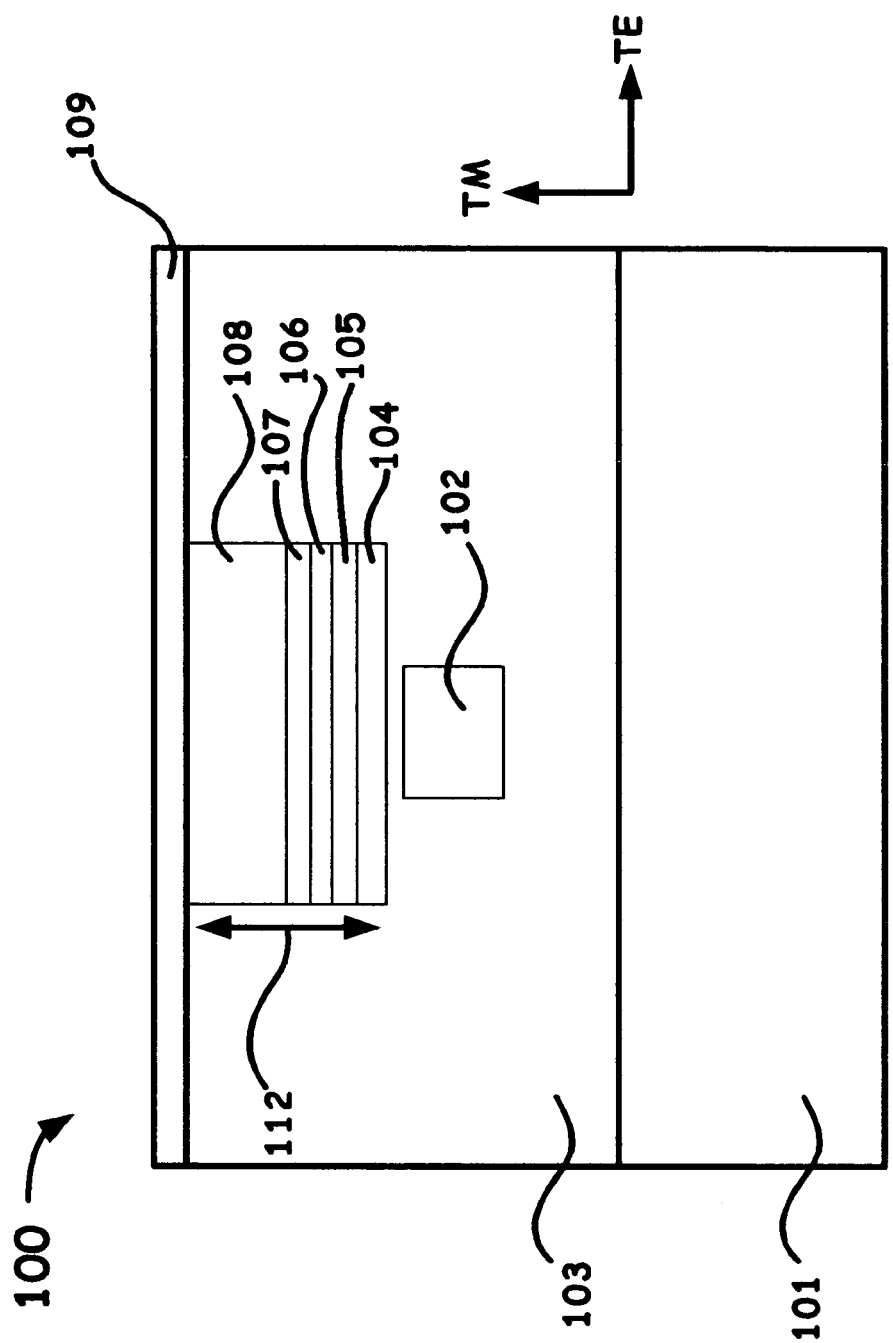
FIG. 1 shows a cross section of a waveguide based surface plasmon resonance sensor.

The detailed description of the specific embodiments, together with the general description of the invention, serves to explain the principles of the invention.

Unless otherwise indicated, all numbers expressing quantities of ingredients, constituents, reaction conditions and so forth are to be understood as being modified in all instances by the term "about". Accordingly, unless indicated to the contrary, the numerical parameters set forth in the specification are approximations that may vary depending upon the desired properties sought to be obtained by the subject matter presented herein. At the very least, and not as an attempt to limit the application of the doctrine of equivalents, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical value, however, inherently contain certain errors necessarily resulting from the standard deviation found in their respective testing measurements.

General Description

The sensor chip includes the combination of a waveguide SPR sensor and a waveguide based interferometer on a single chip. The sensor chip is fabricated by depositing an optical waveguide core material with a thickness ranging from about 2 to about 20 µm with a high index of refraction onto a low index layer or substrate by chemical vapor deposition or a similar process, such as for example, flame hydrolysis. Through mask and etch steps, channel waveguides and other waveguide structures, for example, directional couplers and power splitters, are defined in the core material. An additional low index layer is deposited on top of the waveguide structure and the rest of the SPR chip to complete an optical channel waveguide.

The SPR sensor area is formed by etching down the top index layer to form a trench with dimensions between about 10 and about 100 µm in all directions that is coated with a thin metal film, such as gold or silver ranging in thickness from 0.001 um to 1 um thickness, to provide for the surface plasmon resonance. The sensor area or reservoir is small enough for the detection of chemical or biological agents down to micro-liter volumes, often down to about picoliter volumes. The SPR sensitive area is coated with specific antibodies, proteins, DNA sequences or amino acid sequences to provide for a functional layer that is sensitive and specific to chemical or biological agents of interest. By varying the thickness of the metal film or of the antibody layer enables the present invention to be used for linear detection or for threshold detection of predetermined bio-agents.

The waveguide-based interferometer is fabricated through the formation of the optical waveguide structure as described above. The interferometer structure can include an array of single channel Mach-Zehnder (MZ) waveguide structures or an arrayed waveguide grating structure with a fixed optical path length difference.

In an array of single channel MZ structures, light having a wavelength ranging from about 300 nm to about 2000 nm, and more particularly about 800 nm for a gold metal film, is coupled into the input arm of the MZ waveguide structure. As another embodiment, a material substitution (e.g., silver instead of gold for the plasmon layer) enables a wavelength having a range between about 600 nm and about 650 nm to be deployed without departing from the scope of the invention. However, any wavelength range capable of producing plasmon resonance to the design parameters of the present may also be employed.

The majority of the light passes through the MZ arm with the SPR sensor while the rest of the light is sent through a reference arm of the MZ structure. Amplitude and phase of the light that is transmitted through the SPR sensor is altered for TM polarization and remains relatively unchanged for TE polarization. Amplitude and phase of the light passing through the reference MZ arm remains relatively unchanged. Both polarizations are then combined at the second coupler and the resulting intensity is substantially altered by the amplitude and phase change through SPR sensing waveguide. The MZ interferometer is designed with a built in bias for a predetermined application. A beneficial bias provides a nominal MZ phase shift of $\pi$ radians. Such a design allows the intensity at the output waveguide to be half of the input intensity before any changes occur due to a detection event Therefore, when a target molecule is absorbed by the functional sensing layer, the phase of the light in the SPR leg of the MZ structure is capable of changing by a value of up to $\pi$ radians, and the output intensity drops to about zero. Such a device is beneficial for autonomous detection of biohazards or chemicals above a certain threshold, from which an alarm is capable of being triggered.

To compensate for temperature and mechanical stress induced changes in the MZ interferometer, the TE polarization that is transmitted through the same interferometer can be designed as a reference. The difference of TE vs. TM polarization is independent to any environmental changes and depends only on the sensing scheme. The TE and TM polarizations are capable of being separated and detected either externally through a polarization beam splitter or internally with a built-in waveguide based polarization beam splitter. Other beneficial biases are nominally near $\pi/4$ and $3\pi/4$, placing the amplitude response of the MZ near its greatest slope where the sensitivity of the sensor will be at its greatest A dual SPR cell can be designed and fabricated onto both arms of an MZ interferometer for eliminating the SPR amplitude and phase change due to bulk solution that carries the molecules for detection. However, only the SPR detection cell on the signal arm is functionalized with a capture layer to chemically bond to the target molecules. The SPR reference cell on the reference arm is identical to the SPR detection cell but without the functional sensing layer so that target molecules will not be absorbed to the SPR reference cell. The SPR reference cell is used to cancel the SPR amplitude change and phase shift due to the bulk solution, i.e. solvents, since the identical solution is placed onto both the detection and reference SPR cells. The net change of SPR amplitude and phase is the result of a target molecule being absorbed onto the capture layer of the detection cell. The absence of the SPR reference cell cancels the effect of an index change of the liquid solution due to ambient temperature fluctuations. In consequence, the detection of target molecules is greatly enhanced due to the elimination of a noisy background produced by, for example, such temperature fluctuations.

An SPR sensor based on an array of waveguides with different path-lengths can be produced from an array of SPR sensors arranged with a single waveguide input and output arm. Each waveguide SPR sensor is optically delayed in time, therefore a single scan of an external optical delay line simultaneously measures the amplitude and phase of each SPR sensor. Separation of any interferences from each SPR sensor in the array is achieved by use of a low coherence light source. A SPR reference cell is placed in the shortest optical delayed waveguide. To avoid changes due to temperature fluctuations, the wavelength stabilized light source accurately determines an optical path delay and further extracts the amplitude and phase of each SPR sensor separately. This single input arrayed waveguide SPR sensor simplifies multiple channel detection. A single interferometric scan allows the simultaneous recording of greater than about 1000 SPR sensors.

Specific Description

The sensor of the present invention couples an electromagnetic light source, such as, but not limited to, an LED or a laser, to the waveguide surface plasmon sensor structure as disclosed herein. FIG. 1 shows a cross-sectional view of such a sensor structure as viewed along the propagation direction of the guided light produced from a source (not shown) and is generally designated as reference numeral 100. Light in a wavelength range between about 300 nm and about 2000 nm is operatively coupled into a core high index waveguide 102, surrounded by a cladding material 103 having a lower index of refraction than waveguide 102. Such a cladding material 103 is operatively coupled to a first material 104, having a thickness up to about 100 nm and a predetermined index of refraction higher than cladding material 103. First material 104 is designed to couple the TM polarized wave transmitted through waveguide 102 with a thin metal layer 105, such as, but not limited to gold and silver, having a thickness between about 20 nm and about 100 nm. At resonance frequencies, light having a TM polarization (the TM and TE polarization orientations are denoted and shown by corresponding reference arrows) is absorbed in thin metal layer film 105 and is used to drive surface plasmons, while light with TE polarization remains relatively unchanged. Such resonance frequencies are very sensitive to the configuration of thin metal film 105, a buffer layer 106, a capture layer 107, and a number of target molecules (not shown) in a reservoir 108, which can operatively bind to capture layer 107. A sensor is realized by measuring the frequency shift or by measuring the transmitted light intensity or phase change at a resonance frequency before and after the target molecules (not shown) are absorbed by capture layer 107. A top layer 109 is capable of being bonded by techniques known in the art to cladding material 103 and operates as a seal of sensor 100 for micro-fluidic flow through reservoir 108. Optical structures 102, 103, 104, are made from transparent materials such as silica glass, or another optically transparent material (e.g. polymers), with varying index of refraction. Buffer layer 106 is made from a (typically organic) material, such as dextran that allows for easy deposition of other organic or inorganic materials with functional groups that are highly specific to one or more target molecules (not shown) deposited in reservoir 108.

The fabrication method of the invention for creating sensor 100 includes: etching away cladding material 103 by methods known to those skilled in the art to create a trench 112 (as shown by the respective arrows in FIG. 1) that has a depth less than cladding material 103. Such a trench 112, includes depositing first material 104 having a thickness up to about 100 nm, depositing metal layer 105 having a thickness between about 20 nm and about 100 nm, depositing buffer layer 106, having varying thicknesses up to about 100 nm, and depositing capture layer 107 having a predetermined thickness with predetermined bioagents so as to bind to one or more monolayers, such as antibodies that are deposited in reservoir 108. The entire sensor 100, is arranged on top of a planar support 101, such as a silicon wafer or other material that is capable of meeting design specifications without departing from the scope of the invention.

Figure 2:
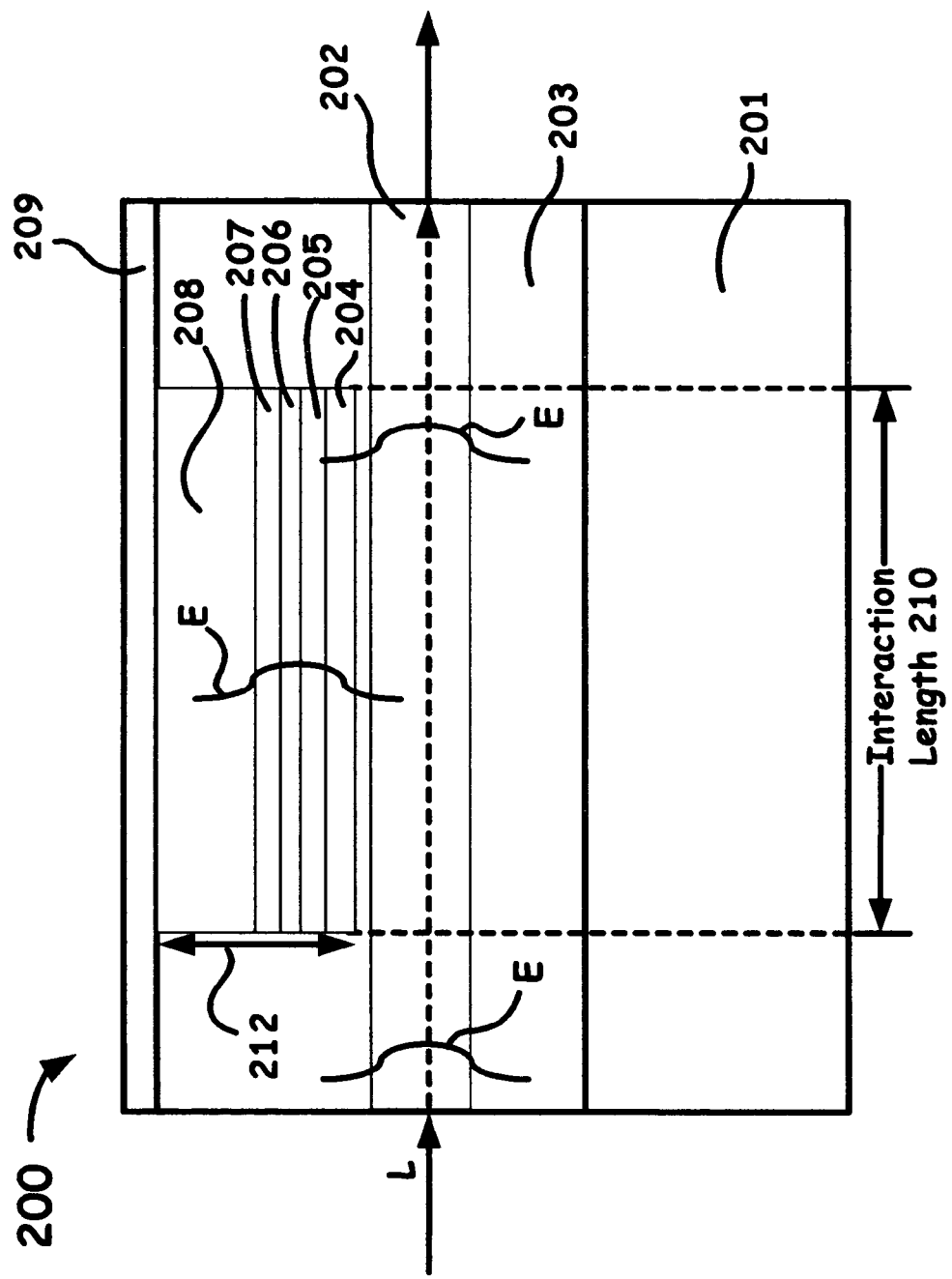
FIG. 2 is a schematic side view of a surface plasmon resonance sensor.

FIG. 2 is a side-view of the waveguide-based surface plasmon resonance sensor as shown in FIG. 1 and is generally designated as reference numeral 200. The first number for each reference number shown in FIG. 2 refers to the same portion reference numeral as shown in FIG. 1 (e.g. 201 is the same layer as 101 from a different point of view). FIG. 2 also shows the direction of the propagation and coupling of light (denoted by the letter E for the e-field and the letter L for the direction as shown with the directional arrows) from a source (not shown) as well as an interaction length 210 that high index waveguide 202 (shown as 102 in FIG. 1) makes with layers 204 and 205 (shown respectively as 104 and 105 in FIG. 1), i.e., the interaction length that the TM field produces surface plasmons.

Figure 3:
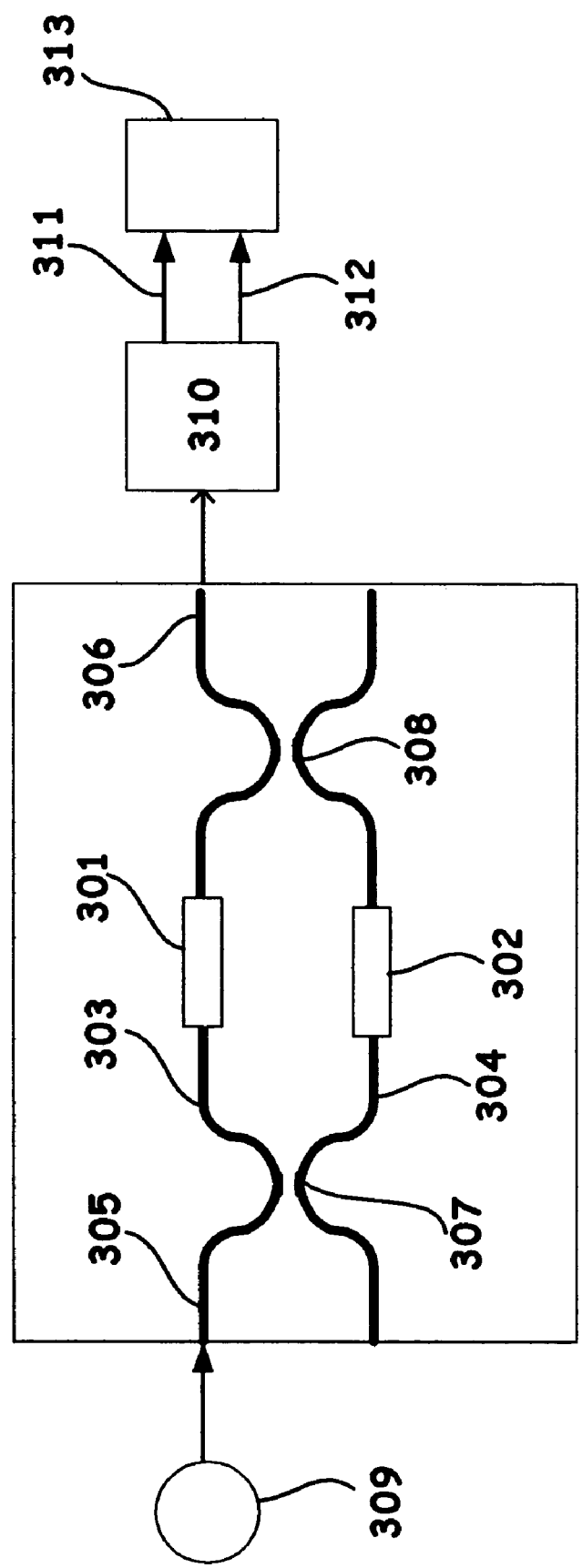
FIG. 3 shows a schematic of a surface plasmon resonance sensor lightwave Mach-Zehnder based interferometry circuit.

As another embodiment, the optical waveguide structure, as shown in FIG. 3, forms an SPR interferometer arranged as a planar waveguide-based SPR Mach-Zehnder interferometer sensor and is generally designated as reference numeral 300. A light source 309, such as an LED or a laser, is coupled into an input waveguide 305 and is directed to a first coupler 307. First coupler 307 is designed at a low coupling ratio such that the majority of the light is transmitted through a signal arm 303 and a SPR sensor 301 on top of which the SPR thin metal film (not shown) is located. The light transmitted through signal arm 303 and SPR detection sensor 301 interferes with the light transmitted through a reference arm 304 and an SPR reference sensor 302. The SPR reference sensor is identical to the SPR detection sensor as described in FIG. 1 and FIG. 2 without the deposition of capture layer 107 and 207. Second coupler 308 is designed to have maximum interference of light from source 309 transmitted through both signal arm 303 and reference arm 304 by taking into account the light loss that occurs in the sensing area of thin metal film 301 and 302. The resulting interference is detected upon transmission through an output waveguide 306. An external optical splitter 310, such as, for example, a bulk polarization splitter, and one or more complementary optical components, such as a high reflectance mirror 310' is arranged to separate and direct the TE 311 and TM 312 polarizations. A measuring means 313, such as, but not limited to, a conventional differential or ratioing detector, is coupled to operatively coupled electronic devices, such as amplification electronic circuits, computers, etc., to enhance signals and perform computations on the respective TM and TE polarizations, e.g., measuring the ratio of such polarizations.

Figure 4:
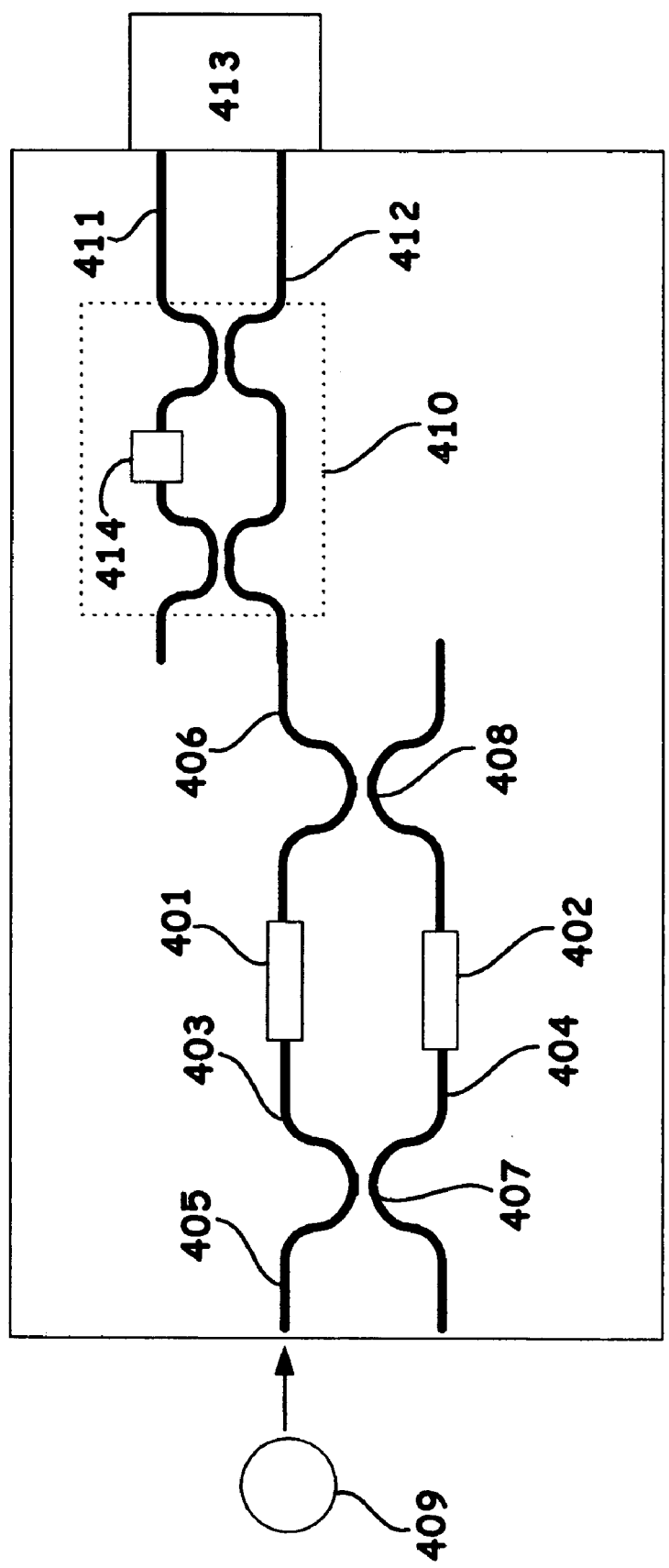
FIG. 4 shows a schematic of a surface plasmon resonance sensor lightwave interferometer circuit with a waveguide based polarization splitter.

FIG. 4 shows another embodiment of a waveguide based SPR interferometer as shown in FIG. 3. The numbers referenced in FIG. 4 are in the same notation as in FIG. 3 with the last number describing the same structure (e.g. 403 is the same as 303). The difference in the sensor design between FIG. 3 and FIG. 4 is the built-in waveguide based polarization splitter 410 (shown enclosed by a dashed box), such as, a birefringence $\pi$ phase shifted optical element 414 in a Mach-Zehnder structure. A pair of output waveguides 411 and 412, separate TE and TM polarizations. The same detection scheme, e.g., a differential or ratioing detector 413, as shown in FIG. 3 is applied for measuring the ratio of TM and TE polarization intensities.

Figure 5A:
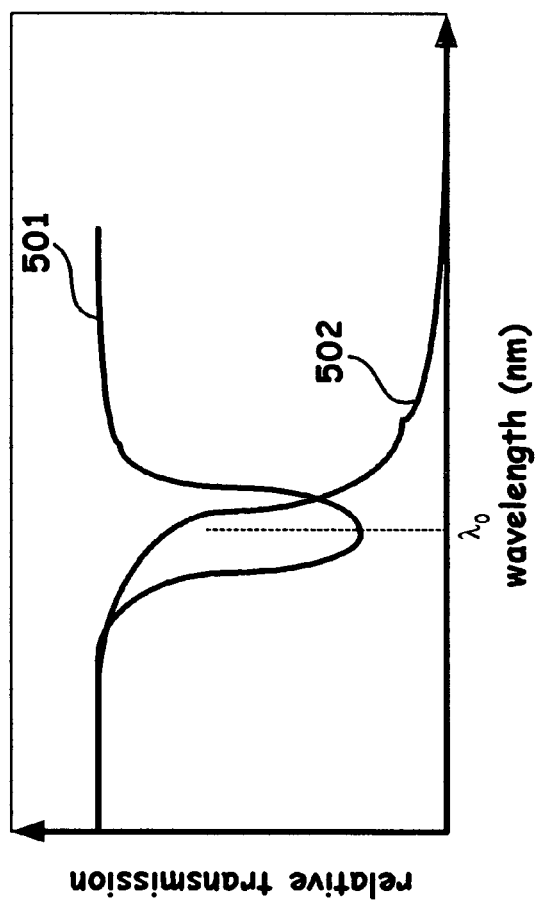
FIG. 5(a) shows the relative transmission of a waveguide surface plasmon resonance sensor versus wavelength with and without interferometer circuits.
Figure 5B:
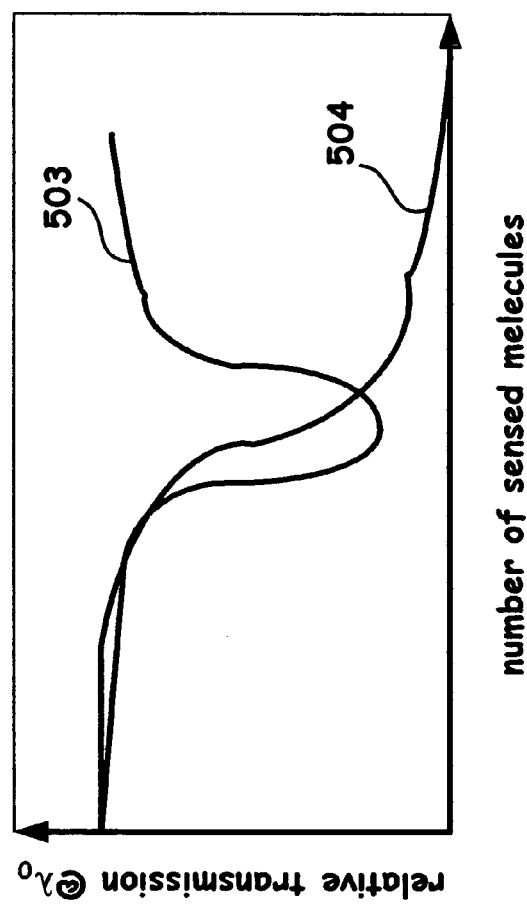
FIG. 5(b) shows the relative transmission of a waveguide surface plasmon resonance sensor versus # of sensing moecules with and without interferometer circuits.

FIG. 5a shows the difference in the signal of a waveguide-based SPR sensor with and without a Mach-Zehnder-based interferometer. Without a Mach-Zehnder interferometer, the wavelength response of the surface plasmon resonance shows a dip 501 in the response curve. Accordingly, the relative transmission at wavelength $\lambda_o$ as function of the number of absorbed target molecules shows non-monotonic behavior, 503 as shown in FIG. 5b. For the sensor with Mach-Zehnder interferometer as shown in FIG. 3 and FIG. 4, the response is a monotonic decrease in transmission as a function of wavelength as shown in 502 of FIG. 5a and as a function of the number of detected target molecules as shown in 504 of FIG. 5b.

Figure 6:
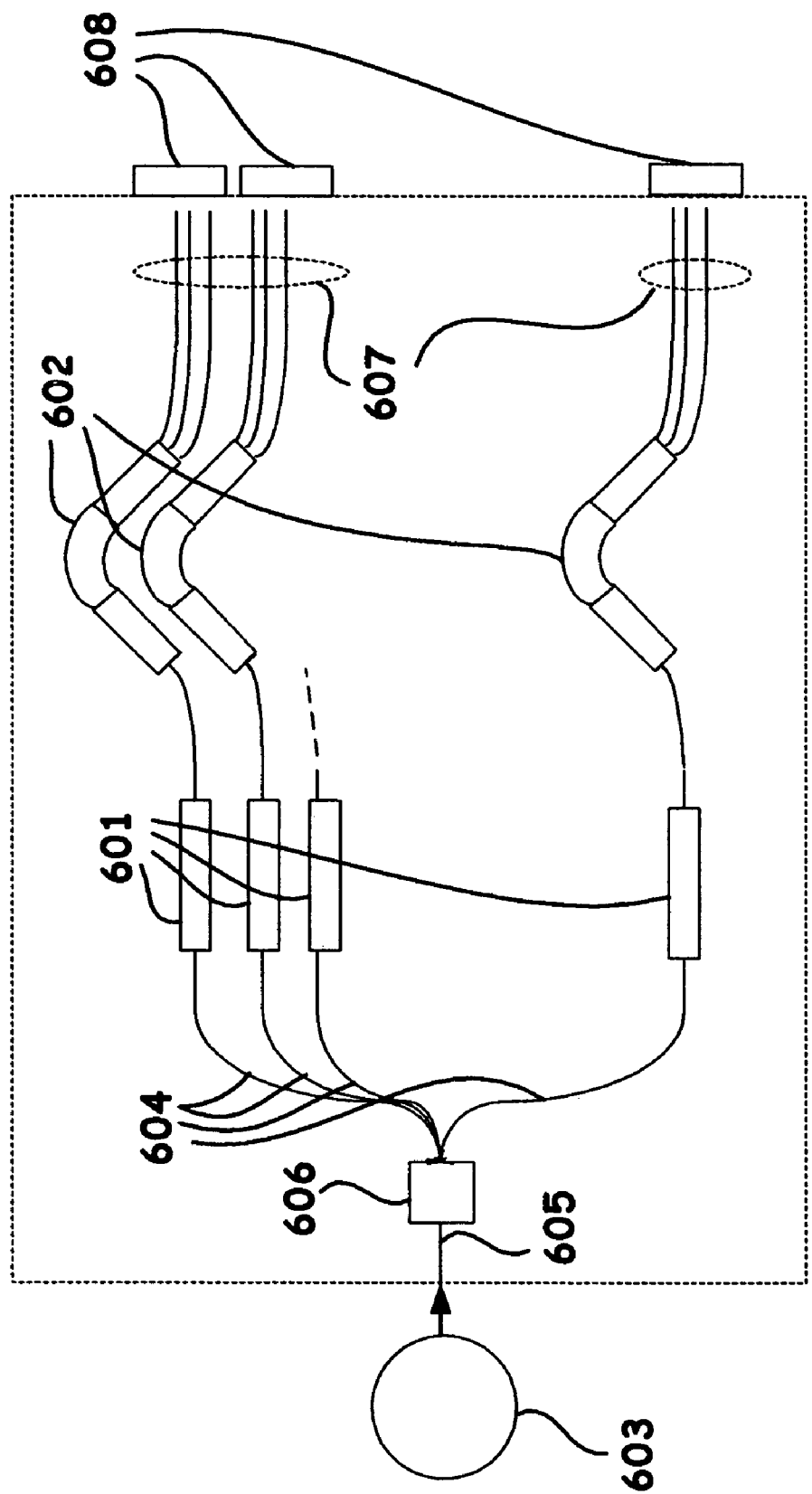
FIG. 6 shows arrays of surface plasmon resonance sensors with waveguide based spectral analyzer.

FIG. 6 shows an array of waveguide SPR sensors 601 with built-in waveguide grating(s) 602 that operate as waveguide-based spectral analyzers. A light source 603 is coupled into an input waveguide 605 and split into one or more arrays of waveguides 604 via a power splitter 606. Light transmitted through waveguides 604 is partially absorbed in SPR sensors 601 where the target molecules (not shown) are detected. One or more arrayed waveguide grating(s) 602 are capable of being placed after sensor 601 for spectral interrogation of the SPR response. An intensity of each wavelength is directed by an array of output waveguides 607 and measured by a detection means 608, such as, but not limited to, an array detector, a photodiode array, a time sensitive detector, a photo-detector, and/or a charge-coupled device structure and is capable of being further analyzed by a microprocessor, e.g., a computer.

Figure 7:
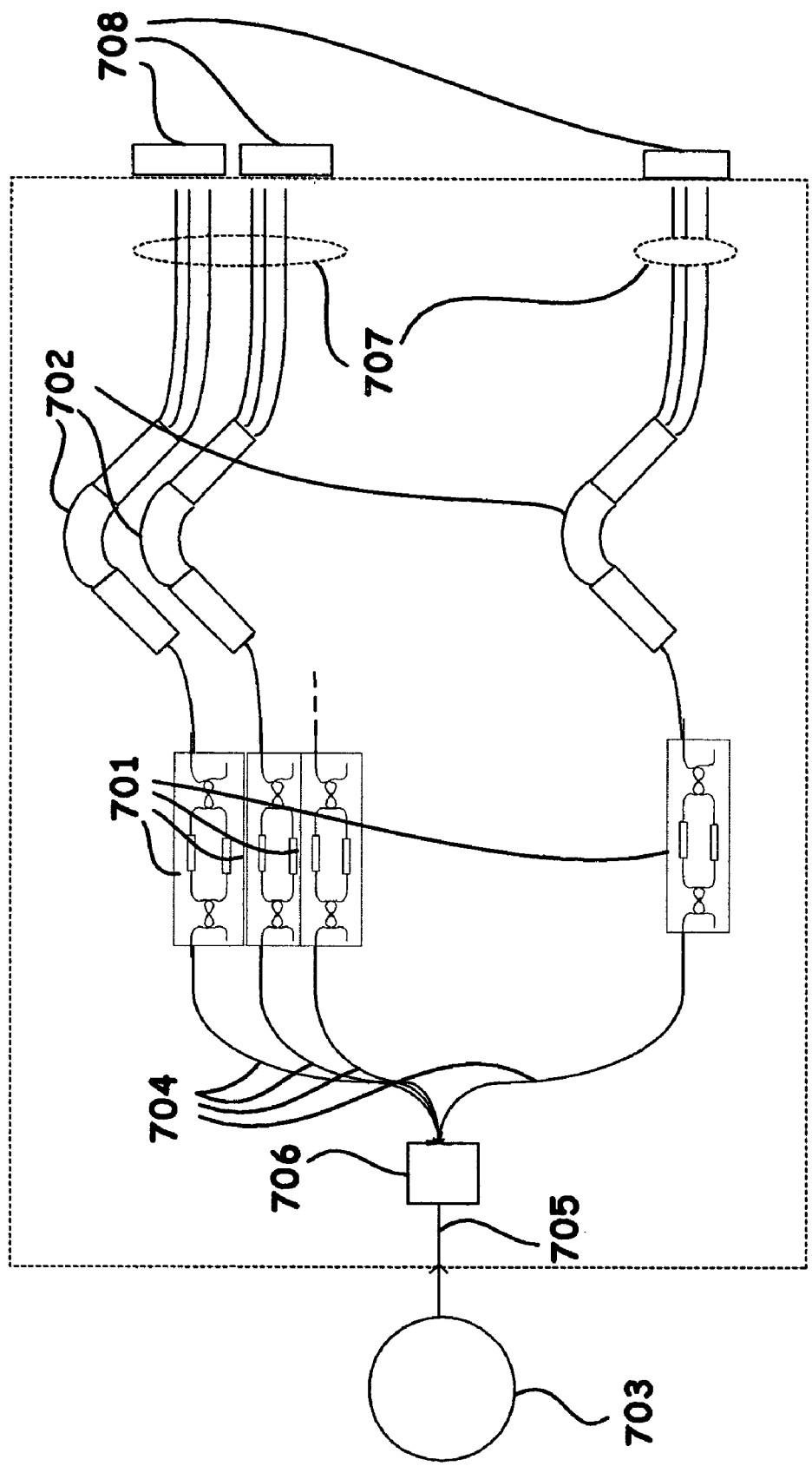
FIG. 7 shows arrays of surface plasmon resonance interferometer sensors with respective waveguide based spectral analyzers.

FIG. 7 is the same spectral interrogation mechanism as shown in FIG. 6. Instead of using surface plasmon resonance sensor 601 as shown in FIG. 6, a Mach-Zehnder interferometer based surface plasmon resonance sensor 701, which is discussed hereinbefore in FIG. 3 and FIG. 4, is substituted to enhance sensitivity. Reference numerals 703, 704, 705, 706, 702, 707, and 708 correspond to the device structures discussed hereinbefore in FIG. 6, i.e., 603, 604, 605, 606, 602, 607, and 608 respectively.

Figure 8A:
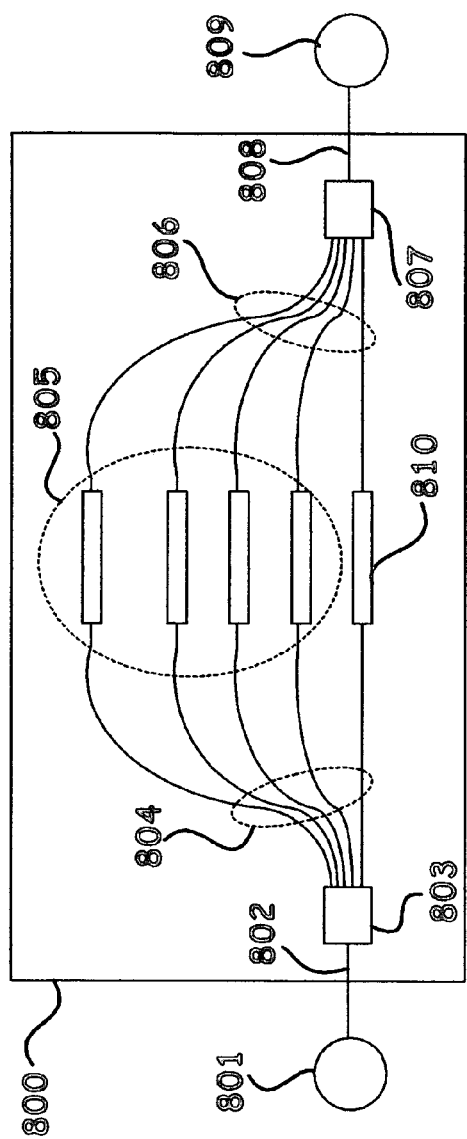
FIG. 8(a) shows a schematic of arrays of surface plasmon resonance sensors in an optical delay configuration.

FIG. 8 shows a structure of optically delayed surface plasmon sensor arrays 800. An arrayed surface plasmon sensor(s) 805 are time delayed through a corresponding array of optical delay lines 804, 806. Light source 801 is received by input waveguide 802 and optical power is split into array of waveguides 804 by a power splitter 803. Array of waveguides 804, have an equal length difference, $\Delta L$, and direct transmission of source 801 to arrayed surface plasmon resonance sensors (SPR) 805 and a SPR reference sensor 810. Optical delay line(s) 806 receives transmitted light by SPR 805 and combines at power combiner 807. The combined light at power combiner 807 is coupled out by an output waveguide 808 and detected by means 809, such as, but not limited to, a time sensitive detector, a photo-detector, and/or a charge-coupled device structure and is capable of being further analyzed by a microprocessor, e.g., a computer.

Figure 8B:
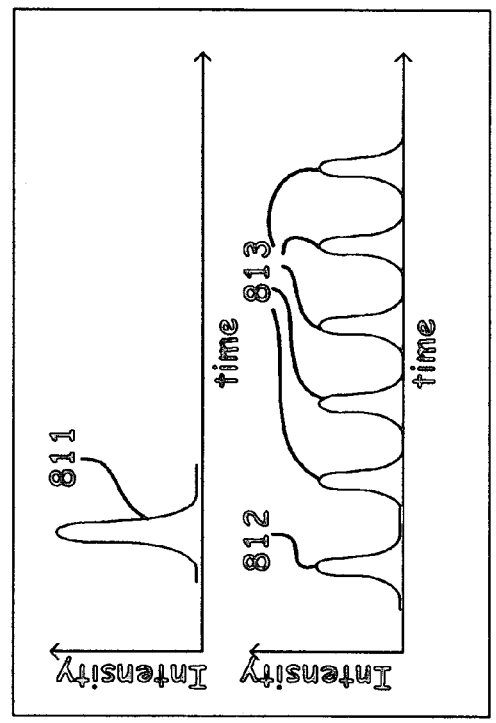
FIG. 8(b) illustrates time profiles of an input short pulse and a resultant measured output.

FIG. 8b, illustrates time profiles of an input short pulse 811 and a resultant measured output 812 and 813. Each time-delayed pulse(s) 813 represents the transmitted light from individual SPR sensor(s) 805 and 812 corresponds to reference SPR 810. The phase and amplitude detection of measured output pulses is capable of sensing, for example, bio-agents, in each of SPR sensor 805 in the array(s).

Figure 9:
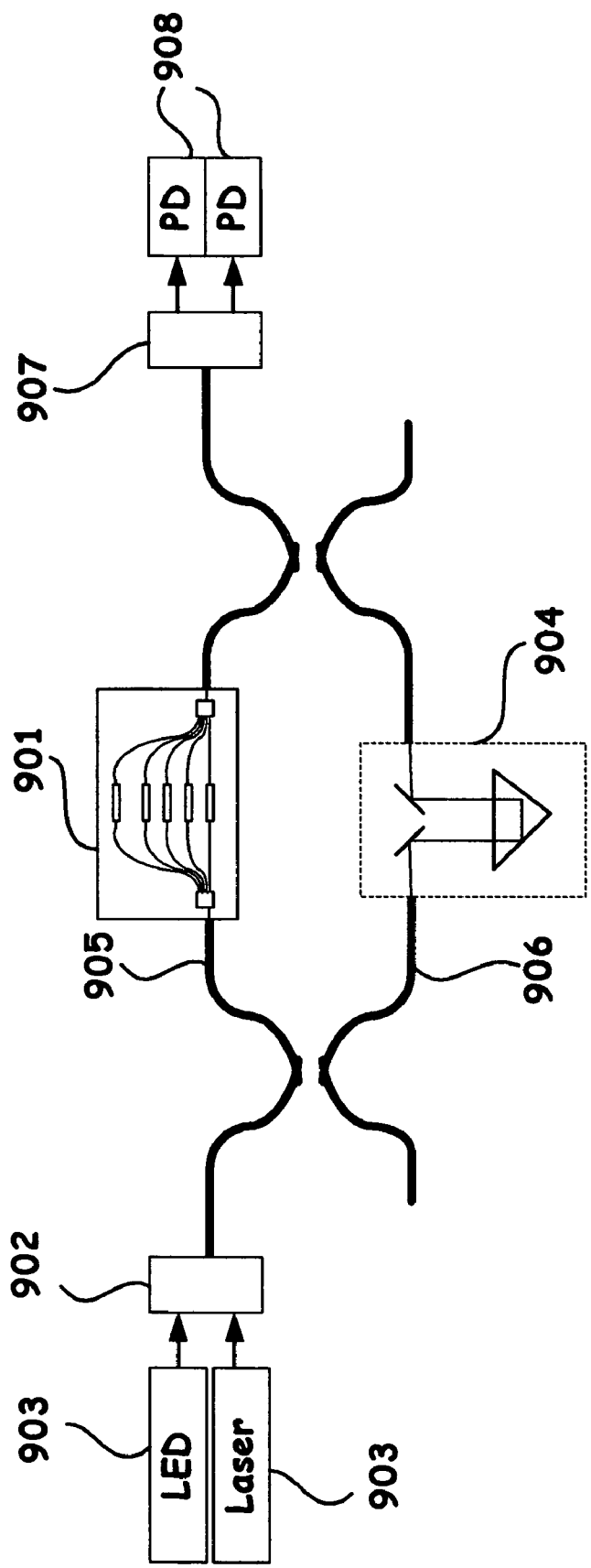
FIG. 9 shows the schematics of a measurement setup using an optical low coherence interferometer for sensing arrays of surface plasmon resonance sensors with optical delay configuration.

The amplitude and phase change in optical delayed surface plasmon sensor arrays 800 also can be detected by an optical low coherence interferometer. FIG. 9 shows an additional embodiment of an optical low coherence interferometer, including a fiber based Mach-Zehnder-based interferometer having an optical delayed array of SPR sensors 901 (shown as 800 in FIG. 8) on signal arm 905 and a variable optical delay element on reference arm 906. The input light sources 903, such as a broadband LED and a narrow line lasers, having at two different wavelengths, can be coupled into an input fiber of 905 by wavelength multi-plexer 902. An optical delay configuration 904, such as, but not limited to, a variable optical delay element or a mechanic optical delay line, is used to resolve the transmission intensity and phase changes resulting from sensing array of SPR sensors 901 from the interference with transmission of reference arm 906. Light having different wavelengths from source 903 are transmitted through the same Mach-Zehnder interferometer but separated by wavelength de-multiplexer 907. The individual interference of both wavelengths can be measured by, for example, a pair of detectors 908, such as photodiodes (PD's). Applicants are providing this description, which includes drawings and examples of specific embodiments, to give a broad representation of the invention. The scope of the invention is not intended to be limited to the particular forms disclosed and the invention covers all modifications, equivalents, and alternatives falling within the spirit and scope of the invention.

The invention claimed is:

1. An apparatus, comprising:
one or more optical channels, comprising a planar waveguide based configuration and further comprising at least one Mach Zehnder (MZ) interferometer arrangement, wherein at least one of said optical channels includes a surface plasmon resonance (SPR) sensor that further comprises:
a substrate,
a core layer,
a cladding arranged to surround said core layer and operatively attached to said substrate, wherein said core layer and said cladding operate as a waveguide,
a trench sensing area, further comprising, a first material, a metal layer operatively attached to said first material, a buffer layer operatively attached to said metal layer, a capture layer operatively attached to said buffer layer, and
wherein a raised portion of said cladding defines a reservoir above said capture layer;
wherein at least one of said optical channels includes a SPR sensor arranged as a reference sensor; and
wherein an optical waveguide arrayed grating is capable of being operatively coupled to a predetermined sensor for spectral interrogation of an SPR response.

2. The apparatus of claim 1, wherein said apparatus includes an optically delayed wave-guide array(s) configuration.

3. The apparatus of claim 1, wherein said capture layer includes one or more monolayers of arranged anti-bodies that bind to one or more deposited chemical and/or bioagents in said reservoir.

4. The apparatus of claim 1, wherein a Transverse Electric (TE) polarization is maximized in a reference output waveguide of said MZ interferometer, while a Transverse Magnetic (TM) polarization in a signal arm waveguide is undergoing a phase shift and an output intensity change from a maximum intensity to a minimum intensity as a result of sensing one or more target agents.

5. The apparatus of claim 4, wherein said TE and a TM polarization are analyzed by a built-in optical waveguide based TE/TM Π shifted Mach-Zehnder polarization splitter.

6. The sensor of claim 1, wherein a layer is fixedly attached to said cladding to seal a predetermined solution in said defined reservoir above said capture layer.

7. An apparatus, comprising:
one or more optical channels arranged in an optically delayed planar waveguide based configuration, wherein at least one of said optical channels includes a surface plasmon resonance (SPR) sensor that further comprises:
a substrate,
a core layer,
a cladding arranged to surround said core layer and operatively attached to said substrate, wherein said core layer and said cladding operate as a waveguide,
a trench sensing area, further comprising, a first material, a metal layer operatively attached to said first material, a buffer layer operatively attached to said metal layer, a capture layer operatively attached to said buffer layer, and
wherein a raised portion of said cladding defines a reservoir above said capture layer; and
wherein at least one of said optical channels includes a SPR sensor arranged as a reference sensor; and
wherein one or more optical arrayed waveguide gratings are capable of being operatively coupled to a predetermined sensor for spectral interrogation of an SPR response of a said predetermined sensor.

8. The apparatus of claim 7, wherein said apparatus is arranged as a low coherence interferometer.

9. The apparatus of claim 8, wherein a phase and an amplitude change of a predetermined sensor is extracted from a resultant interference fringe.

10. The apparatus of claim 7, wherein said apparatus includes a series of SPR sensing antibody arrays that are time delayed through a corresponding array of said optical delay lines.

11. The apparatus of claim 7, wherein said apparatus includes an optical delay line selected from a variable optical delay line and a mechanical optical delay line.

12. The apparatus of claim 7, wherein one or more predetermined optical channels operating as waveguides each have a path length difference, $\Delta L$ greater than a coherence length of a predetermined broadband source.

13. The apparatus of claim 7, wherein said apparatus includes at least one optical power splitter.

14. The apparatus of claim 7, wherein said apparatus includes at least one optical power combiner.

15. The apparatus of claim 7, wherein said apparatus includes a SPR reference sensor on a predetermined optical channel.

16. The apparatus of claim 7, wherein a layer is fixedly attached to said cladding to seal a predetermined solution in said defined reservoir above said capture layer.

17. An apparatus, comprising:
one or more optical channels, comprising a planar waveguide based configuration and arranged as an array of wave-guide surface plasmon resonance (SPR) sensors, wherein each said SPR sensor that further comprises:
a substrate,
a core layer,
a cladding arranged to surround said core layer and operatively attached to said substrate, wherein said core layer and said cladding operate as a waveguide,
a trench sensing area, further comprising, a first material, a metal layer operatively attached to said first material, a buffer layer operatively attached to said metal layer, a capture layer operatively attached to said buffer layer, and
wherein a raised portion of said cladding defines a reservoir above said capture layer; and
wherein an optical waveguide arrayed grating is capable of being operatively coupled to each said sensor for spectral interrogation of an SPR response.

* * * * *